(12) United States Patent
Kerc

(10) Patent No.: US 7,485,322 B2
(45) Date of Patent: Feb. 3, 2009

(54) MODIFIED RELEASE PHARMACEUTICAL COMPOSITION

(75) Inventor: Janez Kerc, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 701 days.

(21) Appl. No.: 10/740,208

(22) Filed: Dec. 18, 2003

(65) Prior Publication Data

US 2004/0131669 A1 Jul. 8, 2004

(30) Foreign Application Priority Data

Dec. 24, 2002 (SI) ............................... 200200318
Sep. 24, 2003 (SI) ............................... 200300246

(51) Int. Cl.
*A61K 9/48* (2006.01)
*A01N 25/34* (2006.01)

(52) U.S. Cl. ..................................... 424/453; 424/408

(58) Field of Classification Search ................ 424/453, 424/408, 438
See application file for complete search history.

(56) References Cited

U.S. PATENT DOCUMENTS

| | | | | | |
|---|---|---|---|---|---|
| 1,815,902 | A | * | 7/1931 | Ellzey | .................. 424/9.45 |
| 2,340,037 | A | * | 1/1944 | Zipper | ........................ 424/453 |
| 3,186,910 | A | * | 6/1965 | Glassman | ................... 53/452 |
| 3,976,764 | A | * | 8/1976 | Watanabe et al. | ........... 424/451 |
| 4,140,755 | A | * | 2/1979 | Sheth et al. | .................. 424/472 |
| 4,601,896 | A | * | 7/1986 | Nugent | ........................ 424/453 |
| 4,681,583 | A | * | 7/1987 | Urquhart et al. | ............. 424/454 |
| 4,814,178 | A | * | 3/1989 | Bolton et al. | ................. 424/467 |
| 5,002,772 | A | * | 3/1991 | Curatolo et al. | .............. 424/438 |
| 5,169,638 | A | * | 12/1992 | Dennis et al. | ................ 424/457 |
| 5,223,265 | A | * | 6/1993 | Wong | ........................... 424/473 |
| 5,232,704 | A | * | 8/1993 | Franz et al. | .................. 424/456 |
| 5,314,696 | A | * | 5/1994 | Paulos | ......................... 424/453 |
| 5,387,421 | A | * | 2/1995 | Amidon et al. | .............. 424/472 |
| 6,015,577 | A | | 1/2000 | Eisert | |
| 7,163,693 | B1 | * | 1/2007 | Clarke et al. | ................. 424/451 |
| 2001/0036473 | A1 | * | 11/2001 | Scott et al. | ................... 424/463 |
| 2003/0194430 | A1 | * | 10/2003 | Miller et al. | ................. 424/451 |

FOREIGN PATENT DOCUMENTS

| | | |
|---|---|---|
| EP | 0714656 | 6/1996 |
| WO | WO98/50019 | 11/1998 |
| WO | WO02/070021 | 9/2002 |

OTHER PUBLICATIONS

K H Bauer, K-L Fromming, C Fuhrer: "Lehrbuch der Pharmazeutischen Technologie", 1999, Wissenschaftliche Verlagsgesellschaft, Stuttgart, XP002278625, p. 340; figure 14.41.

* cited by examiner

*Primary Examiner*—Sharon E. Kennedy
(74) *Attorney, Agent, or Firm*—Luedeka, Neely & Graham, P.C.

(57) ABSTRACT

The present invention relates to a novel modified release pharmaceutical composition comprising the coated capsule body, coated or uncoated capsule cap, at least one tablet and granulate comprising active substance.

44 Claims, No Drawings

MODIFIED RELEASE PHARMACEUTICAL COMPOSITION

This application claims benefit of Slovenian Patent Application No. P-200200318, filed Dec. 24, 2002, and Slovenian Patent Application No. P-200300246, filed Sep. 24, 2003, which in their entirety are herein incorporated by reference.

The present invention belongs to the field of pharmaceutical technology and relates to novel modified release pharmaceutical compositions in the form of floating capsules.

The present invention provides suitable pharmaceutical compositions for drug substances having an absorption window in the upper part of the gastrointestinal tract. There is a constant need to develop new pharmaceutical compositions which retain in the stomach for a predetermined time and enable the controlled release of the drug substance from such pharmaceutical composition in order to enhance the bioavailability of the drug substances with absorption window.

In the literature a number of delivery systems, made by different technologies, provide a pharmaceutical compositions to remain in the stomach for an extended period of time and enable controlled release of the active substance in the upper part of the gastrointestinal tract. Floating pharmaceutical compositions are also one of the options. These compositions have a density that is less than a density of gastric contents. Floating may be enabled by gas liberated in contact with water, hydrogel, generated in contact of a formulation with gastric contents (hydrodynamically balanced floating system) or a low-density core to which the active substance is applied.

U.S. Pat. Nos. 4,140,755; 4,167,558 and 4,424,235 disclose sustained release pharmaceutical formulations freely floating in the gastric fluid for an extended period of time during which substantially all of the active substance is released therefrom. The basis is the hydrodynamically balanced system.

U.S. Pat. No. 4,126,672 discloses uncoated sustained release pharmaceutical capsules comprising a hydrodynamically balanced homogeneous mixture of one or several active substances and at least one hydrophilic colloidal substance which in contact with water forms gel. Preferably hydroxypropylmethylcellulose is used as a hydrocolloid substance.

U.S. Pat. No. 5,198,229 discloses complicated floating capsules having a part containing the active substance, a part containing air or some other gas providing floating, and two separate parts containing inert material which swells upon contact with fluid.

DESCRIPTION OF THE INVENTION

It is an object of the present invention to provide a pharmaceutical composition which has prolonged gastric residence and is suitable for formulating drug substances with an absorption window.

The present invention describes a modified release pharmaceutical composition in a form of a capsule, preferably a floating capsule.

Generally capsules consists of two parts which differ in the length. They also differ slightly in the diameter. The longer and the shorter part of the capsule are considered as a capsule body and a capsule cap, respectively.

The composition of the present invention comprises a coated or uncoated capsule body, coated or uncoated capsule cap, granulate comprising an active substance and at least one tablet optionally comprising active substance. The key of the invention is in the combination of coatings on the body and cap, and in the composition of the granulate and the tablet providing floating of the capsule in gastric fluid for a predetermined period of time upon oral administration and controlled release of the active substance from the granulate and tablet in the capsule. The floating capsule of the invention is a relatively simple delivery system which may be prepared by conventional technological procedures and using conventional technological equipment.

The capsule coating due to insolubility or poor solubility in an aqueous medium prevents influx of water into the capsule for a predetermined period of time and air entrapped by the granulate in the capsule enables floating of the capsule. Generally, the capsule cap is first dissolved, the tablet retains the granulate in the capsule body. During that period of time the active substance is released only from the tablet. When the capsule body is first dissolved, the active substance is first released from granulate. Upon a predetermined period of time the capsule coating and walls disrupt leading to release of the active substance from the granulate and the tablet. Start of the release is controlled by the composition and thickness of a coating. If a cap is uncoated or its coating is dissolved before the coating of the body, release of the active substance starts after the cap is dissolved. Once the release process is initiated, the capsule may still float or remain buoyant for a certain period of time in the medium or it may sink and disintegrate whereat the capsule contents slowly breakup to the basic parts.

The capsule contents consists of a granulate and at least one tablet. The granulate and optionally the tablet contain the active substance. The tablet has a function of keeping/fixing the granulate inside the capsule during the capsule production, handling and oral administration of the capsule. The release rate of the active substance from the capsule also depends on the composition of the granulate and the tablet. In the presence of water the tablet and the granulate form hydrogel and the active substance is slowly released therefrom due to diffusion through the hydrogel and erosion of the hydrogel. The release of the active substance may be controlled by erosion of the lipophilic matrix in case of lipophilic components. The capsule of the invention may comprise one, two or more tablets.

The pharmaceutical composition of the present invention has a wide application for dosing of active substances which have an absorption window in the upper part of the gastrointestinal tract, that is, in the stomach, duodenum and jejunum. Examples of these active substances are some active nucleic acids or amino acids and their derivatives, peptidomimetic substances, antiulcer agents, some analgesics, antipsychotics, antidepressants, antiepileptics, cytostatics, antimigraine agents, antiviral substances, antibiotics, anti-inflammatory agents, sedatives, antidiabetic agents, antihistamines, therapeutic ions, vitamins, bronchodilators, antihypertensives, diuretics, hypolipemic agents, antiobesity agents.

Suitable active substances are, for example, carbidopa, levodopa, methyldopa, verapamil, propranolol, carvedilol, atenolol, albuterol, pirbuterol nifedipine, nimodipine, nicardipine, amlodipine, prazosin, guanabenz, alopurinol, metoprolol, oxprenolol, baclofen, alopurinol, sumatriptan, benazepril, enalapril, lisinopril, captopril, quinapril, moxipril, indolapril, olindapril, retinapril, spirapril, cilazapril, perindopril, ramipril, zofenopril, fosinopril, nitrofurantoin, acyclovir, valacyclovir, AZT, inosine, didanosine, pranobex, tribavirin, vidarabine, simvastatin, pravastatin, atorvastatin, lovastatin, selegiline, midazolam, lithium carbonate or citrate, cimetidine, ranitidine, famotidine, nizatidine, bifentidine, nifentidine, roxatidine, omeprazole, lansoprazole, pentoprazole, antacids such as magnesium carbonate, aluminium carbonate, aluminium hydroxide, magnesium oxide, sucralfate, carbenoloxalone, misoprostol, pirenzepine, telenzepine, bismuth salts, ciprofloxacin, clarithromycin, amoxicillin, cephalexin, and the like, ascorbic acid, folic acid, vitamin E, furosemide, topiramide, hydrochlorothiazide, orlistat.

Their pharmaceutically acceptable salts, esters, pure isomers may also be used.

The dose of the active substance depends on individual active substance. The composition of the present invention is also suitable for the medicaments having high dose of the active substance.

A capsule body and cap may be basically made from polymer-based materials such as, for example, hydroxypropyl methylcellulose, gelatin and starch. Preferably capsules made from hydroxypropylmethylcellulose (HPMC) are used.

A capsule may be completely coated or only a capsule body or only a capsule cap may be coated. A body and a cap may be coated with the same or different coatings. If coatings of the cap and the body are different, one coating should dissolve before another. A coating may be insoluble in acidic medium, poorly soluble in acidic medium, poorly soluble independent of pH or insoluble independent of pH. If a body coating is completely insoluble, a cap should be soluble to provide release of the active substance into an open part of the capsule. If a body cap is completely insoluble, a body should be soluble to enable the release of the active substance from the capsule. If a body coating is partially soluble, a cap may be uncoated, coated with the same coating as a capsule body or coated with a coating which is better soluble than a capsule body coating. If a cap coating is partially soluble, a body may be uncoated, coated with the same coating as a capsule cap or coated with a coating which is better soluble than a capsule cap coating. Start of the release of the active substance depends on the coating composition and thickness.

The coatings insoluble in an acidic medium may be formed from polymers such as cellulose acetate phthalate, cellulose acetate mellitate, cellulose acetate succinate, hydroxypropylmethylcellulose phthalate, hydroxypropylmethylcellulose acetate succinate, carboxymethylcellulose ether, polyvinylacetate phthalate, polyester of styrene and maleic acid copolymer, polyester of vinylether and maleic acid copolymer, vinylacetate and crotonic acid copolymer, copolymers of methacrylic acid and ethylacrylate, copolymer of methacrylic acid and methacrylate, e.g., Eudragit L100, Eudragit L100-55, Eudragit L30D-55, Eudragit S100, or their combinations.

Coatings which are insoluble, irrespective of pH, may comprise ethylcellulose, copolymers of methacrylate/trimethylamonioethylmethacrylate (e.g., Eudragit RL PO, Eudragit RL 100, Eudragit RL30D, Eudragit RS PO, Eudragit RS 100, Eudragit RS30D or their combinations), neutral polymer of methacrylate (e.g., Eudragit NE 30 D, Eudragit NE 40 D) or their combinations.

For poorly soluble coatings there may be used any combinations of the above listed insoluble polymers with soluble polymers such as, for example, combinations of ethylcellulose and hydroxypropylmethylcellulose, hydroxypropylcellulose, hydroxyethylcellulose, methylcellulose or polyvinylpyrrolidone, a combination of methacrylate/trimethylammonio ethylmethacrylate copolymers (e.g., Eudragit RL PO, Eudragit RL 100, Eudragit RL30D, Eudragit RS PO, Eudragit RS 100, Eudragit RS30D or their combinations) and hydroxypropylmethylcellulose, hydroxypropylcellulose, hydroxyethylcellulose or methylcellulose, a combination of neutral methacrylate polymer (e.g., Eudragit NE 30 D, Eudragit NE 40 D) and hydroxypropylmethylcellulose, hydroxypropylcellulose, hydroxyethylcellulose, methylcellulose or polyvinylpyrrolidone.

Coatings may optionally comprise other excipients conventionally used in coatings such as fillers, e.g., talc, lactose, polysaccharides and others, plasticizers, e.g., dibutyl sebacate, triethyl citrate, polyethylene glycol, adipic acid, coconut oil, oleic acid and the like, colorants, e.g., titanium dioxide, lakes, pigments and the like, antioxidants and other excipients. Coatings may optionally comprise bioadhesive polymers.

Particularly suitable coatingts are Acryl-Eze™ (manufacturer Colorcon) and combination of ethylcelullose or Surelease® (manufacturer Colorcon) and hydroxypropylmethylcellulose or hydroxypropylcellulose in the ratio from 80:20 to 10:90. Acryl-Eze™ comprises methacrylic acids and methacrylate copolymer Eudragit L100-55. Surelease® comprises ethylcellulose as a polymer.

Prior to application of a functional coating, a capsule or capsule parts may be coated with a dispersion (solution or suspension) of a hydrophilic polymer, e.g., hydroxypropylmethylcellulose, hydroxypropylcellulose, hydroxyethylcellulose.

The thickness of the coating may vary from 5 to 200 µm, preferably from 10 to 100µm. The thickness of the coating of the capsule body may be the same or different as the thickness of the coating of the capsule cap.

Coatings may be applied by techniques which are conventional for capsule coating in pharmaceutical technology. A coating dispersion may be a solution or suspension of polymers and other excipients. Solvents used for the preparation of the coating-dispersion may be water, ethanol, methanol, propan-2-ole, acetone, ethyl acetate, acetic acid, glycols, dichloromethane, dimehylformamide, dimethylsulfoxide, chloroform, toluene, methylene chloride, benzene, ethoxyethyl acetate, ethylene glycol monoacetate, ethyl lactate, monoethyl acetate, methyl ethyl ketone and their combinations.

Capsules or their parts may be coated empty (before filling) or capsules already filled with the granulate and tablets may be coated.

A granulate contains an active substance and at least one hydrophilic or lipophilic substance which controls the release of the active substance. Polymer or nonpolymer substances may be used. Suitable polymers may be selected from hydroxypropylcellulose, hydroxypropylmethylcellulose, methylcellulose, ethylcellulose, hydroxyethylcellulose, sodium carboxymethylcellulose, cellulose acetate phthalate, polyvinylacetate phthalate, hydroxymethylcellulose phthalate, polyvinylalcohol, polyvinylpyrrolidone, methylhydroxyethylcellulose, polymers and copolymers of acrylic and methacrylic acid, copolymers of ethylacrylate and methylacrylate, maltodextrin, xantham gum, guar gum, acacia, alginic acid and sodium alginate. Suitable nonpolymers may be selected from carnauba wax, cetyl alcohol, hydrogenated vegetable oil, hydrogenated castor oil, glycerol monostearate, glycerol palmitostearate, a mixture of mono-, di- and triglycerides and the like. Preferably hydroxypropylmethylcellulose, methylcellulose and ethylcellulose are used.

The granulate may optionally comprise other excipients such as different fillers, binders, disintegrants, glidants, lubricants and excipients that enhance the absorption of drugs from gastrointestinal tract. Suitable fillers may be selected from microcrystalline cellulose, powdered cellulose, lactose, starch, pregelatinized starch, sucrose, glucose, mannitol, sorbitol, calcium phosphate, calcium hydrogen phosphate, aluminium silicate, sodium chloride, potassium chloride, calcium carbonate, calcium sulphate, dextrates, dextrin, maltodextrin, glycerol palmitostearate, hydrogenated vegetable oil, kaolin, magenesium carbonate, magnesium oxide, polymethacrylates, talc, and others. Preferred fillers are microcrystalline cellulose and lactose. Suitable binders may be starch, pregelatinized starch, gelatine, sodium carboxymethylcellulose, polyvinylpyrrolidone, alginic acid, sodium alginate, acacia, carbomer, dextrin, ehylcellulose, guar gum, hydrogenated vegetable oil, methylcellulose, hydroxyethylcellulose, hydroxypropylcellulose, hydroxypropylmethylcellulose, glucose syrup, magnesium aluminium silicate, maltodextrin, polymethacrylates, zein. Preferably hydroxypropyl cellulose, hydroxypropyl methylcellulose and polyvinylpyrrolidone are used. Suitable disintegrants may be selected from starch, pregelatinized starch, sodium starch glycolate, sodium carboxymethylcellulose, cross-linked sodium carboxymrethylcellulose, calcium carboxymethylcellulose, methylcellulose, microcrystalline cellulose, powdered cellulose, polacrilin potassium, cross-linked polivinylpyrrolidone, alginic acid, sodium alginate, colloidal silicon dioxide, guar gum, magnesium aluminium silicate, and others. Preferred disintegrants are sodium starch glycolate, cross-linked carboxymethylcellulose sodium and cross-linked polyvinylpyrrolidone. Suitable glidants may be magnesium stearate, calcium stearate, aluminium stearate, stearic acid, palmitic acid, cetanol, stearol, polyethylene glycols of different molecular weights, magnesium trisilicate, calcium phosphate, colloidal silicon dioxide, talc, powdered cellulose, starch and others. Preferred glidant is colloidal silicilon dioxide. Suitable lubricants may be selected from stearic acid, calcium, magnesium, zinc or aluminium stearate, siliconized talc, glycerol monostearate, glycerol palmitostearate, hydrogenated castor oil, hydrogenated vegetable oil, mineral oil, light mineral oil, polyethylene glycol, sodium benzoate, sodium lauryl sulphate, sodium stearyl fumarate, talc and others. Preferred lubricants are calcium or magnesium stearate and stearic acid. Suitable absorption enhancers may be selected from surface active agents, fatty acids, middle chain glycerides, steroide detergents (salts of bile salts), acyl carnitine and alcanoloil choline (esters of carnitine and choline and fatty acids with middle chain and long chain), N-acyl derivatrives of alpha-amino acids and N-acyl derivatives of non-alpha-amino acids, chitosanes and other mucoadhesive polymers. Especially suitable absorption enhancers are sodium deoxycholate, sodium taurocholate, polisorbate 80, sodium lauryl sulfate, sodium dodecylsulfate, octanoic acid, sodium docusate, sodium laurate, glyceride monolaurate, stearic acid, palmitinic acid, palmitooleinic acid, glycerilmonooleate, sodium taurocholate, ethylenediaminetetraacetic acid, sodium edentate, sodium citrate, β-cyclodextrine and sodium salicylate.

Granulate may be prepared by techniques conventionally known in the pharmaceutical art for the preparation of granulate, for example, simple mixing of powders (direct mixture), and the dry or wet granulation.

The tablet in the capsule may comprise one or more active substances. Active substances in the tablet may be the same as in the granulate, or may be different. The tablet composition may be qualitatively and expressed by percentage the same as or different from the granulate composition. Optionally, the tablet may be prepared from excipients only without an active substance.

The floating capsule of the present invention may comprise one or more tablets. According to the composition these tablets may be the same or different. Tablets comprising active substance may optionally be combined with tablets comprising only inactive ingredients. Tablets containing different active substances may optionally be used.

The tablet comprises at last one hydrophilic or lipophilic substance which controls the release of the active substance. For this purpose polymer or nonpolymer substances may be used. Suitable polymers include hydroxypropylcellulose, hydroxypropylmethylcellulose, methylcellulose, ethylcellulose, hydroxyethylcellulose, sodium carboxymethylcellulose, cellulose acetate phthalate, polyvinylacetate phthalate, hydroxymethylcellulose phthalate, polyvinylalcohol, polyvinylpyrrolidone, methylhydroxyethylcellulose, polymers and copolymers of acrylic and methacrylic acid, copolymers of ethylacrylate and methylacrylate, maltodextrin, xanthan gum, guar gum, acacia, alginic acid and sodium alginate.

Suitable nonpolymer substances may be carnauba wax, cetyl alcohol, hydrogenated vegetable oil, hydrogenated castor oil, glycerol monostearate, glycerol palmitostearate, a mixture of mono-, di- and in triglycerides and the like. Preferably hydroxypropylmethylcellulose, methylcellulose and ethylcellulose are used.

The tablet may optionally comprise excipients such as, for example, fillers, binders, disintegrants, surfactants, glidants, lubricants and excipients that enhance the absorption of drugs from gastrointestinal tract.

Suitable fillers include microcrystalline cellulose, powdered cellulose, lactose, starch, pregelatinized starch, sucrose, glucose, mannitol, sorbitol, calcium phosphate, calcium hydrogen phosphate, aluminium silicate, sodium chloride, potassium chloride, calcium carbonate, calcium sulphate, dextrates, dextrin, maltodextrin, glycerol palmitostearate, hydrogenated vegetable oil, kaolin, magnesium carbonate, magnesium oxide, polymethacrylates, talc and the like. Preferred fillers are microcrystalline cellulose and lactose. Suitable binders are starch, pregelatinized starch, gelatine, sodium carboxymethylcellulose, polyvinylpyrrolidone, alginic acid, sodium alginate, acacia, carbomer, dextrin ethylcellulose, guar gum, hydrogenated vegetable oil, methylcellulose, hydroxyethylcellulose, hydroxypropylcellulose, hydroxypropylmethylcellulose, glucose syrup, magnesium aluminium silicate, maltodextrin, polymethacrylates, zein. Preferably hydroxypropylcellulose, hydroxypropylmethylcellulose and polyvinylpyrrolidone are used. Suitable disintegrants may be selected from starch, pregelatinized starch, sodium starch glycolate, sodium carboxymethylcellulose, cross-linked sodium carboxymethylcellulose, calcium carboxymethylcelllulose, methylcellulose, microcrystalline cellulose, powdered cellulose, polacrilin potassium, cross-linked polyvinylpyrrolidone, alginic acid, sodium alginate, colloidal silicon dioxide, guar gum, magnesium aluminium silicate and others. Preferably sodium starch glycolate, cross-linked sodium carboxymethylcellulose and cross-linked polyvinylpyrrolidone are used. Suitable glidants may be selected from magnesium stearate, calcium stearate, aluminium stearate, stearic acid, palmitic acid, cetanol, stearol, polyethylene glycols of different molecular weights, magnesium trisilicate, calcium phosphate, colloidal silicon dioxide, talc, powdered cellulose, starch and others. Preferred glidant is colloidal silicon dioxide. Suitable lubricants may be stearic acid, calcium, magnesium, zinc or aluminium stearate, siliconized talc, glycerol monostearate, glycerol palmitostearate, hydrogenated castor oil, hydrogenated vegetable oil, mineral oil, light mineral oil, polyethylene glycol, sodium benzoate, sodium lauryl sulphate, sodium stearyl fumarate, talc and others. Preferred lubricants are calcium or magnesium stearate and stearic acid. Suitable absorption enhancers may be selected from surface active agents, fatty acids, middle chain glycerides, steroide detergents (salts of bile salts), acyl carnitine and alcanoloil choline (esters of carnitine and choline and fatty acids with middle chain and long chain), N-acyl derivatrives of alpha-amino acids and N-acyl derivatives of non-alpha-amino acids, chitosanes and other mucoadhesive polymers. Especially suitable absorption enhancers are sodium deoxycholate, sodium taurocholate, polisorbate 80, sodium lauryl sulfate, sodium dodecylsulfate, octanoic acid, sodium docusate, sodium laurate, glyceride monolaurate, stearic acid, palmitinic acid, palmitooleinic acid, glycerilmonooleate, sodium taurocholate, ethylenediaminetetraacetic acid, sodium edentate, sodium citrate, β-cyclodextrine and sodium salicylate.

Tablets may optionally be coated.

Tablets are prepared using the techniques known in the pharmaceutical technology, that is, by direct tabletting the mixture of powders or by tabletting the granulate which is prepared by the wet or dry granulation.

The present invention is illustrated but in no way limited by the following examples:

EXAMPLE 1

| Granulate: | |
| --- | --- |
| Active substance | 95.0 mg |
| Methocel K100MP | 4.5 mg |
| Mg stearate | 1.0 mg |
| Total weight of granulate | 350 mg |
| Tablet: | |
| Active substance | 95.0 mg |
| Methocel K100MP | 4.5 mg |
| Mg stearate | 1.0 mg |
| Total weight of tablet | 215 mg |
| Total weight of two tablets | 430 mg |
| Capsule: HPMC no. 00 size | |
| Coating of capsule body: Acryl-Eze | 3.478 mg/cm² |
| Capsule cap uncoated | |

Methocel is a trade name for hydroxypropylmethylcellulose

Method of preparation:

The active substance, Methocel and magnesium stearate were homogeneously mixed. A portion of the granulate was compressed into tablets, weight 215 mg. Acryl-eze was suspended in water with constant stirring for 30 minutes to obtain a 20% suspension and sieved through a 0.250 mm screen. The resulting suspension was sprayed over HPMC capsule bodies in a perforated coating drum at about 30° C. to obtain an appropriate amount of coat. Coated capsule bodies were filled with the granulate and two tablets, and closed with uncoated capsule caps.

Float test:

The capsule was placed onto the medium for float testing at 37° C., stirred with a magnetic stirrer at 50 rpm and the floating time of the capsule was observed. medium: 0.1 M HCl; a capsule floats for 24 hours medium: 0.001 M HCl; a capsule floats for 6 hours

EXAMPLE 2

| Granulate: | |
| --- | --- |
| Active substance | 90.0 mg |
| Methocel K100MP | 9.5 mg |
| Mg stearate | 1.0 mg |
| Total weight of granulate | 410 mg |
| Tablet: | |
| Active substance | 90.0 mg |
| Methocel K100MP | 9.5 mg |
| Mg stearate | 1.0 mg |
| Total weight of tablet | 278 mg |
| Capsule: HPMC no. 00 size | |
| Coating of capsule body: Acryl-Eze | 3.478 mg/cm² |
| Capsule cap uncoated | |

Method of preparation:

The active substance, Methocel and magnesium stearate were homogeneously mixed. A portion of the granulate was compressed into tablets, weight 278 mg. Acryl-eze was suspended in water with constant stirring for 30 minutes to obtain a 20% suspension and sieved through a 0.250 mm screen. The resulting suspension was sprayed over HPMC capsule bodies in a perforated coating drum at about 300° C. to obtain an appropriate amount of coat. Coated capsule bodies were filled with the granulate and the tablet, and closed with uncoated capsule caps.

Float test:

The capsule was placed onto the medium for float testing at 37° C., stirred with a magnetic stirrer at 50 rpm and the floating time of the capsule was observed. medium: 0.1 M HCl; s capsule floats for 24 hours medium: 0.001 M HCl; a capsule floats for 6 hours medium: phosphate buffer pH 4.5; a capsule floats for 24 hours

EXAMPLE 3

| Granulate: | |
| --- | --- |
| Active substance | 90.0 mg |
| Methocel K100LV | 9.0 mg |
| Mg stearate | 1.0 mg |
| Total weight of granulate | 420 mg |
| Tablet: | |
| Active substance | 90.0 mg |
| Methocel K100LV | 9.0 mg |
| Mg stearate | 1.0 mg |
| Total weight of tablet | 322 mg |
| Capsule: HPMC no. 00 size | |
| Coating of capsule body: Acryl-Eze | 8.448 mg/cm² |
| Capsule cap uncoated | |

Method of preparation:

The active substance, Methocel and magnesium stearate were homogeneously mixed. A portion of the granulate was compressed into tablets weighing 322 mg. Acryl-eze was suspended in water with constant stirring for 30 minutes to obtain a 20% suspension and sieved through a 0.250 mm screen. The resulting suspension was sprayed over HPMC capsule bodies in a perforated coating drum at about 30° C. to obtain an appropriate amount of coat. Coated capsule bodies were filled with the granulate and the tablet, and closed with uncoated capsule caps.

Float test:

The capsule was placed onto the medium for float testing at 37° C., stirred with a magnetic stirrer at 50 rpm and the floating time of the capsule was observed. medium: 0.1 M HCl; a capsule floats 2 hours, remains buoyant for 6 hours medium: citrate buffer pH 4.5; a capsule floats for 1.5, remains buoyant for 4 hours

EXAMPLE 4

| Granulate: | |
|---|---|
| Active substance | 90.0 mg |
| Methocel K100MP | 4.5 mg |
| Eudragit L100 | 4.5 mg |
| Mg stearate | 1.0 mg |
| Total weight of granulate | 460 mg |
| Tablet: | |
| Active substance | 90.0 mg |
| Methocel K100LV | 9.0 mg |
| Mg stearate | 1.0 mg |
| Total weight of tablet | 300 mg |
| Capsule: HPMC no. 00 size | |
| Coating of capsule body: Acryl-Eze | 8.448 mg/cm² |
| Capsule cap uncoated | |

Method of preparation:

The active substance, Methocel K100LV and magnesium stearate were homogeneously mixed and compressed into tablets, weight 300 mg. The active substance, Methocel K100MP, Eudragit and magnesium stearate were mixed to obtain a homogeneous mixture. Acryl-eze was suspended in water with constant stirring for 30 minutes to obtain a 20% suspension and sieved through a 0.250 mm screen. The resulting suspension was sprayed over HPMC capsule bodies in a perforated coating drum at about 30° C. to obtain an appropriate amount of coat. Coated capsule bodies were filled with the mixture and the tablet, and closed with uncoated capsule caps.

Float test:

The capsule was placed onto the medium for float testing at 37° C., stirred with a magnetic stirrer at 50 rpm and the floating time of the capsule was observed. medium: 0.1 M HCl; a capsule floats for 24hours medium: 0.001 M HCl; a capsule floats for 24 hours

EXAMPLE 5

| Granulate: | |
|---|---|
| Active substance | 90.0 mg |
| Methocel K100MP | 4.5 mg |
| HPMCP HP 50 | 4.5 mg |
| Mg stearate | 1.0 mg |
| Total weight of granulate | 460 mg |
| Tablet: | |
| Active substance | 90.0 mg |
| Methocel K100LV | 9.0 mg |
| Mg stearate | 1.0 mg |
| Total weight of tablet | 300 mg |
| Capsule: HPMC no. 00 size | |
| Coating of capsule body: Acryl-Eze | 8.448 mg/cm² |
| Capsule cap uncoated | |

Method of preparation:

The active substance, Methocel K100LV and magnesium stearate were homogeneously mixed and compressed into tablets, weight 300 mg. The active substance, Methocel K100MP, HPMC HP 50 and magnesium stearate were mixed to obtain a homogeneous mixture. Acryl-eze was suspended in water with constant stirring for 30 minutes to obtain a 20% suspension and sieved through a 0.250 mm screen. The resulting suspension was sprayed over HPMC capsule bodies in a perforated coating drum at about 30° C. to obtain an appropriate amount of coat. Coated capsule bodies were filled with the mixture and the tablet, and closed with uncoated capsule caps.

Float test:

The capsule was placed into the float testing medium at 37° C., stirred with a magnetic stirrer at 50 rpm the floating time of the capsule was observed. medium: 0.1 M HCl; a capsule floats for 24hours medium: 0.001 M HCl; a capsule floats for 24 hours

EXAMPLE 6

| Granulate: | |
|---|---|
| Active substance | 90.0 mg |
| Methocel K100LV | 4.5 mg |
| Avicel PH102 | 4.5 mg |
| Mg stearate | 1.0 mg |
| Total weight of granulate | 440 mg |
| Tablet: | |
| Active substance | 90.0 mg |
| Methocel K100LV | 9.0 mg |
| Mg stearate | 1.0 mg |
| Total weight of tablet | 300 mg |
| Capsule: HPMC no. 00 size | |
| Coating of capsule body: Surelease: HPMC E6 70:30 | 6.879 mg/cm² |
| Capsule cap uncoated | |

Method of preparation:

The active substance, Methocel K100LV and magnesium stearate were homogeneously mixed and compressed into tablets, weight 300 mg. The active substance, Methocel K100LV, Avicel and magnesium stearate were mixed to obtain a homogeneous mixture. HPMC E6 was dissolved in water for 45 minutes and Surelease was suspended in HPMC solution with constant stirring for 10 minutes to obtain a 10% suspension. The resulting suspension was sprayed over HPMC capsule bodies in a perforated coating drum at about 40° C. to obtain an appropriate amount of coat.

Coated capsule bodies were filled with the granulate and the tablet, and closed with uncoated capsule caps.

Float test:

The capsule was placed onto the medium for float testing at 37° C., stirred with a magnetic stirrer at 50 rpm and the floating time of the capsule was observed. medium: 0.001 M HCl; a capsule floats for 4 hours medium: citrate buffer pH 4.5; a capsule floats for 4.5 hours, remains buoyant for 6 hours medium: phosphate buffer pH 4.5; a capsule floats for 4 hours

EXAMPLE 7

| Granulate: | |
|---|---|
| Active substance | 80.0 mg |
| Methocel K100LV | 9.5 mg |
| Avicel PH102 | 9.5 mg |
| Mg stearate | 1.0 mg |
| Total weight of granulate | 420 mg |
| Tablet: | |
| Active substance | 90.0 mg |
| Methocel K100LV | 9.0 mg |
| Mg stearate | 1.0 mg |
| Total weight of tablet | 300 mg |
| Capsule: HPMC no. 00 size | |
| Coating of entire preclosed capsule: Surelease: HPMC E6 70:30 | 7.358 mg/cm$^2$ |

Method of preparation:

The active substance, Methocel K100LV and magnesium stearate were homogeneously mixed and compressed into tablets, weight 300 mg. The active substance, Methocel K100LV, Avicel and magnesium stearate were mixed to obtain a homogeneous mixture. HPMC E6 was dissolved in water for 45 minutes and Surelease was suspended in a HPMC solution with constant stirring for 10 minutes to obtain a 10% suspension. The resulting suspension was sprayed over preclosed HPMC capsules in a perforated coating drum at about 40° C. to obtain an appropriate amount of coat. Coated capsules were opened, filled with the mixture and the tablet, and closed with coated capsule caps.

Float test:

The capsule was placed onto the medium for float testing at 37° C., stirred with a magnetic stirrer at 50 rpm and the floating time of the capsule was observed. medium: phosphate buffer pH 4.5; a capsule floats for 5 hours, remains buoyant for 5.5 hours

EXAMPLE 8

| Granulate: | |
|---|---|
| Active substance | 80.0 mg |
| Methocel K100LV | 9.5 mg |
| Avicel PH102 | 9.5 mg |
| Mg stearate | 1.0 mg |
| Total weight of granulate | 560 mg |
| Tablet: | |
| Active substance | 80.0 mg |
| Methocel K100LV | 9.5 mg |
| Avicel PH102 | 9.5 mg |
| Mg stearate | 1.0 mg |
| Total weight of tablet | 180 mg |
| Capsule: HPMC no. 00 size | |
| Coating of capsule body: Surelease: HPMC E6 60:40 Capsule cap uncoated | 6.510 mg/cm$^2$ |

Method of preparation:

The active substance, Avicel and magnesium stearate were homogeneously mixed. A portion of the granulate was compressed into tablets, weight 180 mg. HPMC E6 was dissolved in water for 45 minutes and Surelease was suspended in a HPMC solution with constant stirring for 10 minutes to obtain a 10% suspension. The resulting suspension was sprayed over HPMC capsule bodies in a perforated coating drum at about 40° C. to obtain an appropriate amount of coat. Coated capsules bodies were filled with the granulate and the tablet, and closed with uncoated capsule caps.

Float test:

The capsule was placed onto the medium for float testing at 37° C., stirred with a magnetic stirrer at 50 rpm and the floating time of the capsule was observed. medium: 0.001 M HCl: a capsule floats for 3 hours, remains buoyant for 4 hours medium: phosphate buffer pH 4.5; a capsule floats for 2 hours, remains buoyant for 3 hours

EXAMPLE 9

| Granulate: | |
|---|---|
| Active substance | 80.0 mg |
| Methocel K100LV | 9.5 mg |
| Avicel PH102 | 9.5 mg |
| Mg stearate | 1.0 mg |
| Total weight of granulate | 560 mg |
| Tablet: | |
| Active substance | 80.0 mg |
| Methocel K100LV | 9.5 mg |
| Avicel PH102 | 9.5 mg |
| Mg stearate | 1.0 mg |
| Total weight of tablet | 180 mg |
| Capsule: HPMC no. 00 size | |
| Coating of capsule body: Surelease: HPMC E6 70:30 Capsule cap uncoated | 6.879 mg/cm$^2$ |

Method of preparation:

The active substance, Avicel and magnesium stearate were homogeneously mixed. A portion of the granulate was compressed into tablets, weight 180 mg. HPMC E6 was dissolved in water for 45 minutes and Surelease was suspended in a HPMC solution with constant stirring for 10 minutes to obtain a 10% suspension. The resulting suspension was sprayed over HPMC capsule bodies in a perforated coating drum at about 40° C. to obtain an appropriate amount of coat. Coated capsules bodies were filled with the granulate and the tablet, and closed with uncoated capsule caps.

Float test:

The capsule was placed onto the medium for float testing at 37° C., stirred with a magnetic stirrer at 50 rpm and the floating time of the capsule was observed. medium: 0.001 M HCl: a capsule floats for 2 hours, remains buoyant for 5 hours medium: phosphate buffer pH 4.5; a capsule floats for 4.5 hours, remains buoyant for 5 hours

EXAMPLE 10

| Granulate: | |
|---|---|
| Active substance | 80.0 mg |
| Methocel K100LV | 9.5 mg |
| Avicel PH102 | 9.5 mg |
| Mg stearate | 1.0 mg |
| Total weight of granulate | 560 mg |

-continued

| Tablet: | |
|---|---|
| Active substance | 80.0 mg |
| Methocel K100LV | 9.5 mg |
| Avicel PH102 | 9.5 mg |
| Mg stearate | 1.0 mg |
| Total weight of tablet | 180 mg |
| Capsule: HPMC no. 00 size | |
| Coating of capsule body:<br>EC:HPC 60:40 | 6.500 mg/cm$^2$ |
| Ethylcellulose | 15.240 mg |
| Hydroxypropylcellulose | 10.160 mg |
| Trietyl citrate | 2.298 mg |
| Titanium dioxide | 7.756 mg |
| Talc | 2.546 mg |
| Ethanol | 384.222 mg |
| Capsule cap uncoated | |

Method of preparation:

The active substance, Methocel, Avicel and magnesium stearate were homogeneously mixed. A portion of the granulate was compressed into tablets, weight 180 mg. Hydroxypropylcellulose, ethylcellulose and triethyl citrate were dissolved in ethanol and the resulting solution was added to the suspension of titanium dioxide and talc in ethanol and the suspension was homogenized. The resulting suspension was sprayed over HPMC capsule bodies in a perforated coating drum at about 30° C. to obtain an appropriate amount of coat. Coated capsules bodies were filled with the granulate and the tablet, and closed with uncoated capsule caps.

Float test:

The capsule was placed onto the medium for float testing at 37° C., stirred with a magnetic stirrer at 50 rpm and the floating time of the capsule was observed. medium: phosphate buffer pH 4.5; a capsule floats for 4.5 hours, remains buoyant for 5 hours

The invention claimed is:

1. A modified release pharmaceutical composition in the form of a capsule, the capsule comprising:
    a capsule body
    a coated or uncoated capsule cap,
    at least one tablet and
    a granulate
    wherein the capsule body and cap are assembled so as to encapsulate at least the tablet and granulate together with trapped gas and at least an exposed portion of the capsule body of the assembled capsule is coated with a coating which is substantially insoluble or poorly soluble in an acidic aqueous medium wherein the assembled capsule floats or at least remains buoyant in the acidic aqueous medium for at least about an hour.

2. The pharmaceutical composition according to claim 1 where the granulate comprises a pharmaceutically active substance.

3. The pharmaceutical composition according to claim 1 wherein the tablet and the granulate comprise a pharmaceutically active substance.

4. The pharmaceutical composition according to claim 3 wherein the pharmaceutically active substance is selected from the pharmaceutically active substances having an absorption window in the upper part of the gastrointestinal tract.

5. The pharmaceutical composition according to claim 4 wherein the active substance is selected from the group consisting of antihypertensives, peptidomimetic substances. antiulcer agents, Analgesics, antipsychotics, antidepressants, antiepileptics, cytostatics, antimigraine agents, antiviral substances, antibiotics, anti-inflammatory agents, sedatives, antidiabetic agents, antihistamines, vitamins, bronchodilators, diuretics, hypolipemic agents, antiobesity agents, and combinations of one or more of thereof.

6. The pharmaceutical composition according to claim 1 wherein the capsule body and the cap comprise hydroxypropyl methylcellulose.

7. The pharmaceutical composition according to claim 1 wherein the capsule body is coated with a coating which is insoluble in an acidic medium.

8. The pharmaceutical composition according to claim 1 wherein the capsule cap is coated with a coating which is insoluble in an acidic medium.

9. The pharmaceutical composition according to claim 1 wherein the capsule body is coated with a coating which is insoluble independent of pH.

10. The pharmaceutical composition according to claim 1 wherein the capsule cap is coated with a coating which is insoluble independent of pH.

11. The pharmaceutical composition according to claim 1 wherein the capsule body is coated with a coating which is poorly soluble in an acidic medium.

12. The pharmaceutical composition according to claim 1 wherein the capsule cap is coated with a coating which is poorly soluble in an acidic medium.

13. The pharmaceutical composition according to claim 1 wherein the capsule body is coated with a coating which is poorly soluble independent of pH.

14. The pharmaceutical composition according to claim 1 wherein the capsule cap is coated with a coating which is poorly soluble independent of pH.

15. The pharmaceutical composition according to claim 1 wherein the capsule body is coated with a coating which is a combination of insoluble and soluble polymers.

16. The pharmaceutical composition according to claim 1 wherein the capsule cap is coated with a coating which is a combination of insoluble and soluble polymers.

17. The pharmaceutical composition according to claim 1 wherein the capsule cap is coated with a coating which is better soluble than a coating of the capsule body.

18. The pharmaceutical composition according to claim 1 wherein the capsule body is coated with a coating which is better soluble than a coating of the capsule cap.

19. The pharmaceutical composition according to claim 1 wherein the capsule body and cap are coated with substantially the same coating and wherein the coating is sparingly soluble in acidic medium and the material comprising the capsule body and cap are more soluble than the coating.

20. The pharmaceutical composition according to claim 1 wherein the capsule body coating comprises copolymers of acrylic and methacrylic acid.

21. The pharmaceutical composition according to claim 1 wherein the capsule cap comprises copolymers of acrylic and methacrylic acid.

22. The pharmaceutical composition according to claim 1 wherein the capsule body coating comprises a combination of ethylcellulose and hydroxypropylmethylcellulose.

23. The pharmaceutical composition according to claim 1 wherein the capsule cap coating comprises a combination of ethylcellulose and hydroxypropylmethylcellulose.

24. The pharmaceutical composition according to claim 1 wherein the capsule body coating comprises a combination of ethylcellulose and hydroxypropylcellulose.

25. The pharmaceutical composition according to claim 1 wherein the capsule cap coating comprises a combination of ethylcellulose and hydroxypropylcellulose.

26. The pharmaceutical composition according to claim 1 wherein the capsule body is coated and the capsule cap uncoated.

27. The pharmaceutical composition according to claim 1 wherein the capsule cap is coated and the capsule body uncoated.

28. The pharmaceutical composition according to claim 1 wherein the granulate comprises at least one lipophilic or hydrophilic substance.

29. The pharmaceutical composition according to claim 1 wherein the granulate comprises hydroxypropylmethylcellulose.

30. The pharmaceutical composition according to claim 1 wherein the granulate optionally comprises a material selected from the group consisting of fillers, binders, disintegrants, glidants, lubricants, excipients, and combinations of one or more thereof.

31. The pharmaceutical composition according to claim 1 wherein the composition of the tablet is substantially the same as the composition of the granulate.

32. The pharmaceutical composition according to claim 1 wherein the composition of the tablet is different from the composition of granulate.

33. The pharmaceutical composition according to claim 1 wherein the tablet comprises at least one lipophilic or hydrophilic substance.

34. The pharmaceutical composition according to claim 1 wherein the tablet comprises hydroxypropylmethylcellulose.

35. The pharmaceutical composition according to claim 1 wherein the tablet optionally comprises a material selected from the group consisting of fillers, binders, disintegrants, glidants, lubricants, excipients, and combinations of one or more thereof.

36. The pharmaceutical composition according to claim 1 wherein the tablet does not contain an active substance.

37. The pharmaceutical composition according to claim 1 which comprises one, two or more tablets positioned in the capsule body so as to impede any flow of aqueous medium through a open end of the body into a closed end thereof containing the granulate upon dislodgment of the can from the body and/or dissolution of at least part of the cap in contact with the aqueous medium.

38. The pharmaceutical composition according to claim 37 wherein the composition of all tablets is the same.

39. The pharmaceutical composition according to claim 37 wherein the composition of the tablets is different.

40. The pharmaceutical composition according to claim 37 wherein the tablets contain different active substances.

41. A capsule containing a pharmaceutical composition for release of contents into the upper gastrointestinal tract which comprises a capsule body assembled with a capsule cap to sealably encapsulate therein at least one tablet, granulate, and an amount of a gaseous material and to substantially isolate the tablet, granulate, and gaseous material from an environment surrounding the assembled capsule wherein at least the capsule body or the capsule cap of the assembled capsule is substantially insoluble in aqueous acidic medium with a remaining part of the capsule having at least a slow solubility in the aqueous acidic medium so that the assembled capsule floats adjacent the surface of the aqueous medium for at least about one hour for controlled release of material from inside the capsule into the medium while the capsule remains floating or at least buoyant in the medium.

42. The capsule of claim 41 wherein the capsule body in the assembled capsule includes a coating over at least its exposed outside surface of a material which is substantially insoluble in the aqueous acidic medium.

43. The capsule of claim 41 wherein the material is selected from the group consisting of copolymers of acrylic and methacrylic acid and a combination of ethylcellulose and hydroxypropylmethycellulose.

44. The capsule of claim 41 wherein the tablet or the granulate comprise an active pharmaceutical substance selected from the group consisting of antihypertensives, peptidomimetic substances, antiulcer agents, analgesics, antipsychotics, antidepressants, antiepileptics, cytostatics, antimigraine agents, antiviral substances, antibiotics, anti-inflammatory agents, sedatives, antidiabetic agents, antihistamines, vitamins, bronchodilators, diuretics, hypolipemic agents, antiobesity agents, and combinations of one or more of thereof.

* * * * *